United States Patent
Erdrich et al.

(10) Patent No.: US 6,575,750 B2
(45) Date of Patent: *Jun. 10, 2003

(54) DENTAL EMBEDDING MATERIAL, DENTAL KIT AND METHOD FOR MAKING A PROSTHESIS

(75) Inventors: Albert Erdrich, Bad Nauheim (DE); Frank Stange, Usingen (DE); Novica Savic, Wehrheim (DE); Bettina Korthaus, Schmitten (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 44 days.

This patent is subject to a terminal disclaimer.

(21) Appl. No.: 09/732,388

(22) Filed: Dec. 7, 2000

(65) Prior Publication Data

US 2001/0020051 A1 Sep. 6, 2001

(30) Foreign Application Priority Data

Dec. 9, 1999 (DE) .......................... 199 59 514

(51) Int. Cl.$^7$ .................. A61C 13/34; A61C 13/08; C08L 33/12; C08J 3/28; C08F 2/50
(52) U.S. Cl. .................. 433/202.1; 433/213; 433/214; 522/83; 522/84; 522/85; 522/117; 522/121; 522/908; 206/63.5
(58) Field of Search .................. 522/83, 79, 92, 522/95, 96, 102, 103, 117, 121, 908, 84, 85; 433/202.1, 213, 214, 228.1; 206/63.5; 106/35

(56) References Cited

U.S. PATENT DOCUMENTS

| | | | |
|---|---|---|---|
| 6,103,779 A | * | 8/2000 | Guzauskas |
| 6,353,039 B1 | * | 3/2002 | Rheinberger et al. ....... 523/109 |
| 6,426,373 B1 | * | 7/2002 | Stange et al. ............ 433/202.1 |
| 2001/0020052 A1 | * | 9/2001 | Erdrich et al. .............. 523/112 |

FOREIGN PATENT DOCUMENTS

| | | |
|---|---|---|
| DE | 36 39 067 A1 | 5/1987 |
| DE | 195 02 751 A1 | 8/1996 |
| DE | 299 20 415 U1 | 5/2000 |
| EP | 0 142 172 A2 | 5/1985 |
| GB | 916075 | 12/1959 |
| GB | 1113722 | 5/1965 |

* cited by examiner

Primary Examiner—Susan W. Berman
(74) Attorney, Agent, or Firm—Norris McLaughlin & Marcus

(57) ABSTRACT

Among other things, a dental embedding material is proposed, containing:

- 10–30 wt.-% polyethylene glycol dimethacrylate
- 40–55 wt.-% polymethyl methacrylate
- 5–15 wt.-% highly disperse silicon dioxide
- <1 wt.-% photoinitiators, stabilizers,
- 10–30 wt.-% of at least one compound from the group: urethane dimethacrylate, bis-GMA, ethoxylated bis-GMA.

27 Claims, No Drawings

DENTAL EMBEDDING MATERIAL, DENTAL KIT AND METHOD FOR MAKING A PROSTHESIS

The invention relates to a transparent dental embedding material, a dental kit, a method for making a prosthesis, uses of the embedding material, a prosthesis, an individual flask, a dental pre-rim material. In dental technology a number of traditional methods are known for the production of prostheses.

In DE 195 02 751 A1 a method is disclosed for the production of plastic models for dentistry, in which a photosetting material is used.

GB 1,113,722 A describes an air-curing composition on the basis of mono or bis-acrylate or methacrylate monomers.

GB 916,075 A describes a method for preparing a cast composite article of polymerized methyl methacrylate resin.

In EP 0 142 172 A2 a polymerizable composition is disclosed which consists of a polar organic composition from the group of acids and their salts, a multifunctional vinyl crosslinking composition, and a solvent composition.

DE 36 39 067 A1 describes a method for making a dental plate in which photopolymerizing resins of different viscosities are used for direct formation within a short period of time of a dental plate in an appropriate manner with improved accuracy of fit, and the impression material used is a doughy product of photopolymerizing resins with different viscosities.

In DE 299 20 415 U1 a dental interspacing varnish is described which has a binding agent content of 5 to 60% of a polyvinyl alcohol, color pigments and a volatile alcohol miscible with water.

In the traditional method, on the one hand what is involved is the investment of a trial fitting in plaster of Paris in which the plaster of Paris is mixed with water and is poured over the trial fitting in a curette. After the plaster sets, the wax is boiled out and the plaster surfaces are isolated with alginate. The cavity formed can then be filled with thermally or chemically initiated plastic by the injection method, casting method or ramming method, and the material is polymerized by various methods. A disadvantage of this method is the relatively great expenditure of time and the fact that no visual control is possible to determine whether the flask has been completely filled. It is furthermore disadvantageous that no photopolymerizing materials can be used. In this process the plaster of Paris dries out with the attending changes in volume (shrinkage), while furthermore residual moisture in the plastic can cause discoloration of the plastic and in general a sealing with alginate is necessary.

Another method is the investment of the trial fitting in a hydrocolloid, wherein the hydrocolloid material, or also agar-agar, is liquefied by heating at temperatures above +50° C. and then pouring it over the trial fitting in a flask. After the material has cooled and solidified the wax is removed and the cavity formed is filled with a 2-K autopolymer by the casting method. The 2 components of the autopolymer react by hardening onto the mixture and form the desired raw form of the prosthesis. A disadvantage of this method is the fact that this is a method that is error-prone, in which special flasks are necessary, and generally provides poor deflasking accuracy, and no polymerization is possible above 50° C. It is a disadvantage that this method is suitable only for use with very fluid casting plastics, resulting in greater shrinkage after polymerization.

Lastly, the use of pre-rim silicone is known in partial prosthetic work such as completions in which silicone is modeled in the vestibule onto the trial fitting, cured on the corresponding model, and thus fixes the teeth in their position. Immediately thereafter casting plastic can be poured through the half-side opening and polymerized. A disadvantage in this process is the fact that the silicone has to be mixed from base and hardener, and wrong mixture ratios often result in defective hardening. Commercial condensation crosslinking silicones used for this purpose are transparent, but since they are tacky they cannot be mixed by hand.

Especially those silicones which crosslink by condensation are subject to shrinkage by losing water, and this can lead to prosthesis misfits. Furthermore, the time the silicones require for curing until they are usable is as much as 10 minutes, and furthermore the teeth must be fixed in the silicone by gluing with adhesives containing cyanoacrylate or wax.

From what is said above, the problem arises of how to overcome the above-named disadvantages by means of a novel dental investment material, a dental kit, a method for making a prosthesis, various uses of the investment material, as well as a prosthesis. The problem consists especially in designing a dental investment material which will assure optimum deflasking and accuracy of fit combined with advantageous material and handling properties.

This problem is solved according to the invention by a transparent investment material, a dental kit comprising this material, a method for making a prosthesis comprising this material, additional uses or prostheses made of this material, an individual flask having this material and a dental pre-rim material.

The dental investment material contains 10–30 weight-% polyethylene glycol dimethacrylate, 40–55 weight-% polymethyl methacrylate, 5–15 weight-% highly disperse silicon dioxide, <1 weight-% photoinitiators, stabilizers, 0–10 weight-% polyethylene glycol and 10–30 weight-% of at least one compound from the group, urethane dimethacrylate, bis-GMA, and ethoxylated bis-GMA, and is highly transparent.

The investment material has optimum deflasking accuracy and accuracy of fit in setting up an individual flask, and the term, "individual flask," is to be understood as a cured dental investment material, especially a dental investment material according to the invention, which has been modeled over the work, including teeth, set up in wax. The cavity forming between the plaster of Paris base and the individual flask after removal of the wax can then be filled up with a commercial casting plastic. Due to the great transparency of the individual flask it is possible to use photopolymerizing material as the casting plastic.

The investment material according to the invention has a very high deflasking accuracy and fitting accuracy. Furthermore, the material has a certain elasticity, but on the other hand it is sufficiently brittle to permit easy removal of the individual flask or pre-rim by mechanically shattering the material.

In comparing the investment material of the invention with the known addition-crosslinking, transparent silicones (see DE 40 05 570 A1) the following is to be found:

The known transparent silicones are two-component systems consisting of base and catalyst which are combined with great losses of high-cost raw materials when they are mixed and worked (including the change of the so-called static mixer on the cartridges etc.), while the investment material of the invention is only a single-component material which can be cured by exposure to light, which is taken from the package and applied directly. Since it is soluble in water in the unpolymerized state, it is easy to clean the hands and tools.

While the ratio of admixture and environmental conditions have an influence on the properties of the known silicones even after they are cured, such influence cannot be detected.

The working time of the investment material of the invention can be varied by applying the light accordingly.

Addition crosslinking silicones contain proportions of oxygen in the material which create an inhibiting layer at the interface with the plastic, and such silicones outgas hydrogen for a period after they are made, which can lead to inhomogeneities in the plastic. These disadvantages are not present in the investment material of the invention.

The known silicones have limited hardness (Shore A 65–90) combined with very great flexibility, while the investment material has sufficient elasticity together with greater hardness and consequently it can more easily be broken in the deflasking process (shattering of an individual flask or pre-rim).

Lastly, in the case of the silicones, bonding additional silicone to existing silicone or bonding plastic to silicone is chemically impossible, and furthermore teeth must be fastened with adhesive wax or cyanoacrylate glue, while in the investment material the bonding on of additional acrylates and methacrylates is possible and the gluing in of teeth is not essential.

The above-mentioned advantages also apply to an additional advantageous embodiment of the investment material of the invention, which contains 15–20 wt.-% of polyethylene glycol dimethacrylate, up to 50 wt.-% of polymethyl methacrylate, 10–15 wt.-% of at least one compound from the group urethane dimethacrylate, bis-GMA (2,2-bis(4-(2-hydroxy-3-methacryloyloxypropoxy)phenyl)propane), ethoxylated bis-GMA, (ethoxylated 2,2-bis(4-(2-hydroxy-3-methacryloyloxypropoxy)phenyl)propane), and 10–13 wt.-% highly disperse silicon dioxide, 0.4–0.6 wt.-% photoinitiators, stabilizers, and 5–10 wt.-% polyethylene glycol.

Lastly, the following embodiments have proven advantageous in practice:

The polyethylene glycol dimethacrylate has a mass >500 g/mol.

The polyethylene glycol dimethacrylate is solid at a temperature of about T=+20° C.

The polymethyl methacrylate has a molecular mass of >160,000, an average grain size of 80–140 μm and a benzoyl peroxide content <0.1 wt.-%.

The polymethyl methacrylate is a copolymer which has been made with up to 10 wt.-% of comonomers.

The polyethylene glycol is fluid at a temperature of about T=+20° C. and has an average molar mass of >=200 g/mol.

The urethane dimethacrylate has a minimum molecular mass at the level of 450 g/mol.

Advantageously the polymethyl methacrylate is in the form of suspension polymer, since due to its spherical configuration it provides the investment material with uniform properties.

The dental kit according to the invention contains at least one investment material according to the invention.

The dental kit advantageously contains a dental isolation material which contains 10–60 wt.-% water, 30–85 wt.-% $C_2$–$C_4$ alcohol, 2–10 wt.-% polyvinyl alcohol and 0–30 wt.-% acetone, since in this manner not only the positive properties of the investment material of the invention can be achieved but also good film-forming properties can be obtained by means of the isolation material.

The following variations have proven advantageous in practice:

The isolating material contains 40–50 wt.-% water, 45–55 wt.-% $C_2$–$C_4$ alcohol, 3–8 wt.-% polyvinyl alcohol and 0–5 wt.-% acetone.

The $C_2$–$C_4$ alcohol is ethanol.

The polyvinyl alcohol has a molecular mass of >60,000 g/mol.

In the one method of the invention for the preparation of a prosthesis, first a dental trial fitting is encased by means of an investment material according to the invention to construct an individual flask or pre-rim, and polymerized (cured) by the action of electromagnetic radiation, especially by means of visible light and/or ultraviolet light. Then the inside of the polymerized investment material is coated with an isolating material in order then to be filled with a dental plastic. The latter is then cured especially by electromagnetic radiation, but it can also be configured as an autopolymer. Then the prosthesis is removed by breaking apart the investment material.

The following embodiments have proven advantageous in actual practice:

The dental isolation material contains 10–60 wt-% water, 30–85 wt.-% $C_2$–$C_4$ alcohol, 2–10 wt.-% polyvinyl alcohol, and 0–30 wt.-% acetone, since in this manner not only the positive properties of the investment material of the invention but also good film forming properties can be achieved by means of the isolating material.

The isolation material contains 40–50 wt.-% water, 45–55 wt.-% $C_2$–$C_4$ alcohol, 3–8 wt.-% polyvinyl alcohol and 0–5 wt.-% acetone.

The $C_2$–$C_4$ alcohol is ethanol.

The polyvinyl alcohol has a molecular mass of >60,000 g/mol.

As described above, in this method of the invention, not only is an isolation material of the invention used, but in addition an investment material according to the invention is used advantageously in order not only to separate the cured prosthesis plastic from the individual flask or rim, but also to obtain excellent deflasking accuracy and accuracy of fit.

The prostheses made by this method have, for the above reasons, excellent deflasking accuracy and accuracy of fit.

Advantageously, a dental material which can be cured by electromagnetic radiation, especially by means of visible light and/or UV radiation, is used as dental plastic, because in this manner controlled curing can be achieved by controlled irradiation of the dental plastic.

At the same time it is advantageous to set up retentions prior to coating. The term "retentions" is to be understood in the context of the invention to mean junctions and adjustments, such as chamfering, pins or grooved junctions which prevent tilting, shifting or slippage of the bonding of the plaster base to the individual flask, and thus serve to assure a reversible fit.

Even in the case of conventional methods and/or prosthetic materials for the production of a prosthesis (see above), excellent deflasking and accuracies of fit are to be expected from the use of the investment material of the invention.

Also the individual flasks and pre-rim materials containing the dental investment material of the invention have the above advantageous properties.

In the method of the invention for preparing a prosthesis, the title, "Modeling a Dental Trial Fitting by Means of an Embedding Material," is intended to cover not only the direct modeling of a dental trial fitting, but also the modeling of a dental trial fitting previously coated with a layer of silicone coated in turn with a layer of an adhesive system, as for example an adhesive containing cyanoacrylate.

Lastly, the use of an embedding material to make a model of a transparent plaster substitute is advantageous, since the possibility thus exists of using light to cure the dental plastic poured between the model and the polymerized embedding material (where the trial fitting had previously been), also from the inside of the model, resulting in a very uniform cure.

In brief, the following characteristic properties and advantages of the embedding material of the invention can be summed up as follows:

Optimum modelability, minimized polymerization shrinkage, high transparency, sufficient elasticity, no excessive brittleness, easy destructibility by shattering and cutting, water-soluble dispersion layers that can be washed away, and toxicological acceptability.

The following example will serve to explain the invention:

In the standard procedure, the work is set up in wax, with teeth, on a plaster base. The plaster base is provided with retentions (edges, grooves or pins). The paste-like "individual flask material" is modeled over the trial fitting. 2 to 3 casting openings are created on the back. Then polymerization is performed in a photopolymerization apparatus. The wax is boiled out and the interior of the mold is treated with liquid foil. After drying, the teeth held in the flask material can be normally conditioned. Then the upper part of the flask and the plaster base are again carefully fitted and, for example, set with adhesive wax. Then the casting plastic can be cast and polymerized variously according to the nature of the material. The deflasking is performed by breaking up the individual flask.

With the use of transparent silicone:

Furthermore, the combination of a support (e.g., made of photoconductive methacrylate, for example the above embedding material, or a thermoplastic) with a layer of silicone is conceivable. In this case the silicone is applied to the trial fitting and curing is awaited. Then an adhesive system and the support material—the light-curing methacrylate system is applied. The rest of the procedure is performed as described above.

| Embedding material (flask material) | | |
| --- | --- | --- |
| Urethane dimethacrylate Plex 6661 | Röhm | 12.5 wt.-% |
| Polyethylene glycol-1000-dimethacrylate | Röhm | 18.2 wt.-% |
| Polyethylene glycol 200 | Aldrich | 7.8 wt.-% |
| C-13-methacrylic acid ester | Röhm | 1.9 wt.-% |
| Aerosil R974 | Degussa | 9.0 wt.-% |
| Aerosil 380 | Degussa | 2.0 wt.-% |
| PMMA suspension polymer M 286 | Röhm | 48.0 wt.-% |
| Lucirin TPO | BASF | 0.6 wt.-% |
| Separation material: | | |
| Polyvinyl alcohol 100000 | Fluka | 5.0 wt.-% |
| Deionized water | Kulzer | 45.0 wt.-% |
| Ethanol | Brenntag | 50.0 wt.-% |
| Silicones: | | |
| Crosslinking polyvinyl siloxane Memosil CD | HKKG | 100. wt.-% |

What is claimed is:

1. Transparent dental embedding material, containing:
   10–30 wt.-% polyethylene glycol dimethacrylate
   40–55 wt.-% polymethyl methacrylate
   5–15 wt.-% highly disperse silicon dioxide photoinitiators and stabilizers, together, constituting no more than 1 wt.-%,
   0–10 wt.-% polyethylene glycol and
   10–30 wt.-% of at least one compound selected from the group consisting of:
   urethane dimethacrylate, 2,2-bis(4-(2-hydroxy-3-methacryloyloxypropoxy)phenyl)propane (bis-GMA), ethoxylated-2,2-bis(4-(2-hydroxy-3-methacryloyloxypropoxy)phenyl)propane (ethoxylated bis-G MA],
   wherein the wt.-% values are based on the total weight of the embedding material.

2. Transparent dental embedding material of claim 1, containing:
   15–20 wt.-% polyethylene glycol dimethacrylate
   50 wt.-% polymethyl methacrylate
   10–15 wt.-% of at least one compound selected from the group consisting of:
   urethane dimethacrylate, 2,2-bis(4-(2-hydroxy-3-methacryloyloxypropoxy)phenyl)propane (bis-GMA), ethoxylated-2,2-bis(4-(2-hydroxy-3-methacryloyloxypropoxy)phenyl)propane (ethoxylated bis-G MA],
   10–13 wt.-% highly disperse silicon dioxide photoinitiators and stabilizers, together, constituting no more than 1 wt.-%,
   5–10 wt.-% polyethylene glycol,
   wherein the wt.-% values are based on the total weight of the embedding material.

3. Transparent dental embedding material according to 1, characterized in that the polyethylene glycol dimethacrylate has a molecular mass greater than 500 g/mol.

4. Transparent dental embedding material according to claim 1, characterized in that the polyethylene glycol dimethacrylate is solid at a temperature of about T=+20° C.

5. Transparent dental embedding material according to claim 1, characterized in that the polymethyl methacrylate has a molecular mass of >160,000, an average grain size of 80–140 μm and a benzoyl peroxide content <0.1 wt.-%.

6. Transparent dental embedding material according to claim 1, characterized in that the polymethyl methacrylate is a copolymer which has been made with up to 10 wt.-% of comonomers.

7. Transparent dental embedding material according to claim 1, characterized in that the polyethylene glycol is fluid at a temperature of about T=+20° C. and has an average molecular mass of $\geq$200 g/mol.

8. Transparent dental embedding material according claim 1, characterized in that the urethane dimethacrylate has a molecular mass equal to or greater than 450 g/mol.

9. Transparent dental embedding material according to claim 1, characterized in that the polymethyl methacrylate is in the form of a suspension polymer.

10. The embedding material of claim 1, wherein the embedding material is photopolymerizable and is in a form suitable for preparing full or partial prostheses.

11. The embedding material according to claim 1, wherein the embedding material is in a form suitable for at least one of the following purposes:
   preparing individual flasks, or
   serving as rim material.

12. Dental kit, containing at least one embedding material according to claim 1.

13. Dental kit according to claim 12, characterized in that it has a dental separation material containing:
   10–60 wt.-% water
   30–85 wt.-% $C_2$–$C_4$ alcohol
   2–10 wt.-% polyvinyl alcohol
   0–30 wt.-% acetone.

14. Dental kit according to claim 12, characterized in that it has a dental separation material containing:
- 40–50 wt.-% water
- 45–55 wt.-% $C_2$–$C_4$ alcohol
- 3–8 wt.-% polyvinyl alcohol
- 0–5 wt.-% acetone.

15. Dental kit according to claim 12, characterized in that in the dental separation material the $C_2$–$C_4$ alcohol is ethanol.

16. Dental kit according to claim 12, characterized in that in the dental separation material the polyvinyl alcohol has a molecular mass of >60,000 g/mol.

17. Method for making a prosthesis with the following steps:
   a) modeling over a dental trial fitting with an embedding material according to claim 1 to construct an individual flask or rim,
   b) curing the embedding material by electromagnetic irradiation,
   c) coating the inside of the polymerized embedding material with a dental separation material,
   d) casting the individual flask or rim with a dental plastic, and
   e) deflasking by breaking up the embedding material.

18. Method according to claim 17, characterized in that the dental separation material contains:
- 10–60 wt.-% water,
- 30–85 wt.-% $C_2$–$C_4$ alcohol,
- 2–10 wt.-% polyvinyl alcohol and
- 0–30 wt.-% acetone.

19. Method according to claim 17, characterized in that the dental separation material contains:
- 40–50 wt.-% water
- 45–55 wt.-% $C_2$–$C_4$ alcohol,
- 3–8 wt.-% polyvinyl alcohol,
- 0–5 wt.-% acetone.

20. Method according to claim 17, characterized in that in the dental separation material the $C_2$–$C_4$ alcohol is ethanol.

21. Method according to claim 17, characterized in that in the dental separation material the polyvinyl alcohol has a molecular mass of >60,000 g/mol.

22. Method according to claim 17, characterized in that the dental plastic can be cured by electromagnetic radiation.

23. Method according to claim 17, characterized in that after the over-modeling and before coating, retentions are set up.

24. The method of claim 17 wherein the embedding material is photopolymerizable and is in a form suitable for preparing full or partial prostheses.

25. Prosthesis, characterized in that it has been made by a method of claim 17.

26. Individual flask, containing a dental embedding material according to claim 1.

27. Dental pre-rim material, containing a dental embedding material according to 1.

* * * * *